United States Patent
Chazal et al.

(10) Patent No.: US 8,816,271 B2
(45) Date of Patent: Aug. 26, 2014

(54) DEVICE FOR EMITTING A FIRST BEAM OF HIGH-ENERGY PHOTONS AND A SECOND BEAM OF LOWER-ENERGY PHOTONS, AND ASSOCIATED METHOD AND MEASURING UNIT

(75) Inventors: Damien Chazal, Paris (FR); Pierre-Arnaud Foucher, Poissy (FR); Gérard Segeral, Gif sur Yvette (FR)

(73) Assignee: Geoservices Equipements, Roissy en France (FR)

( * ) Notice: Subject to any disclaimer, the term of this patent is extended or adjusted under 35 U.S.C. 154(b) by 640 days.

(21) Appl. No.: 13/133,962

(22) PCT Filed: Dec. 7, 2009

(86) PCT No.: PCT/FR2009/052427
§ 371 (c)(1),
(2), (4) Date: Aug. 2, 2011

(87) PCT Pub. No.: WO2010/066994
PCT Pub. Date: Jun. 17, 2010

(65) Prior Publication Data
US 2011/0278445 A1    Nov. 17, 2011

(30) Foreign Application Priority Data
Dec. 12, 2008 (FR) .................................... 08 58549

(51) Int. Cl.
*G01V 5/08* (2006.01)

(52) U.S. Cl.
USPC ............... 250/269.1; 250/503.1; 250/269.3; 250/258; 378/147; 378/149

(58) Field of Classification Search
CPC ............ G01V 5/04; G01V 5/08; G01V 5/10; G01V 5/12
USPC ......... 250/269.1, 503.1, 269.3, 258; 378/147, 378/149
See application file for complete search history.

(56) References Cited

U.S. PATENT DOCUMENTS

| | | | |
|---|---|---|---|
| 4,228,353 A * | 10/1980 | Johnson .................... | 250/356.1 |
| 4,450,576 A | 5/1984 | Lubecki | |
| 4,788,852 A | 12/1988 | Martin et al. | |
| 5,822,390 A | 10/1998 | Hewitt et al. | |

(Continued)

FOREIGN PATENT DOCUMENTS

| | | |
|---|---|---|
| CN | 1309768 | 8/2001 |
| CN | 1618258 | 5/2005 |

(Continued)

OTHER PUBLICATIONS

Decision on grant for the equivalent Russian patent application No. 2011128725 issued on Nov. 12, 2013.

*Primary Examiner* — David Porta
*Assistant Examiner* — Djura Malevic
(74) *Attorney, Agent, or Firm* — Cameron R. Sneddon (57) ABSTRACT

This device comprises a single radioactive source (44), capable of creating an incident beam (120), and a target (48) placed opposite the source (44).
The target (48) is capable of creating the second beam (130) by interacting with a first part of the incident beam (120), a second part of the incident beam (120) passing through the target (48) to form the first beam (124).

14 Claims, 5 Drawing Sheets

(56) References Cited

U.S. PATENT DOCUMENTS

| | | | |
|---|---|---|---|
| 5,854,820 A | 12/1998 | Slijkerman et al. | |
| 6,265,713 B1 * | 7/2001 | Berard et al. | 250/269.3 |
| 6,272,934 B1 * | 8/2001 | Rajan et al. | 73/861.04 |
| 6,335,959 B1 * | 1/2002 | Lynch et al. | 378/45 |
| 6,389,108 B1 * | 5/2002 | Ein-Gal | 378/147 |
| 6,389,908 B1 * | 5/2002 | Chevalier et al. | 73/861.63 |
| 6,755,086 B2 * | 6/2004 | Salamitou et al. | 73/861.04 |
| 6,776,054 B1 * | 8/2004 | Stephenson et al. | 73/861.63 |
| 6,776,235 B1 * | 8/2004 | England | 166/271 |
| 7,162,005 B2 * | 1/2007 | Bjorkholm | 378/57 |
| 7,542,543 B2 * | 6/2009 | Shampine et al. | 378/56 |
| 7,639,781 B2 * | 12/2009 | Shampine et al. | 378/54 |
| 7,645,994 B2 | 1/2010 | Tang et al. | |
| 2007/0291898 A1 * | 12/2007 | Groves et al. | 378/51 |
| 2008/0069301 A1 * | 3/2008 | Shampine et al. | 378/53 |
| 2011/0049345 A1 * | 3/2011 | Roberts | 250/269.6 |

FOREIGN PATENT DOCUMENTS

| | | |
|---|---|---|
| EP | 0166914 | 1/1986 |
| EP | 0696354 | 3/1997 |
| FR | 2454619 | 11/1980 |

* cited by examiner

DEVICE FOR EMITTING A FIRST BEAM OF HIGH-ENERGY PHOTONS AND A SECOND BEAM OF LOWER-ENERGY PHOTONS, AND ASSOCIATED METHOD AND MEASURING UNIT

The present invention relates to a device for emitting a first beam of high-energy photons and a second beam of lower-energy photons, of the type comprising:

a single radioactive source, suitable for generating an incident beam of high-energy photons.

Such a device is in particular used to measure phase fractions of a polyphase fluid circulating in a hydrocarbon exploitation pipe, such as an oil or natural gas well, as described for example in U.S. Pat. No. 4,788,852.

To that end, it is known to determine the individual fractions of the gaseous phase, the aqueous liquid phase and the oily liquid phase of the polyphase fluid by emitting a first beam of high-energy photons and a second beam of lower-energy photons. These beams are directed through the fluid to interact therewith.

A detector placed opposite the emitting source collects the photons from the first beam and the second beam to count the number of high-energy photons and the number of low-energy photons having passed through the fluid per unit of time.

Based on these counts, and on a suitable calibration, the fractions of the different phases of the polyphase fluid are calculated.

To create both a beam of high-energy photons and a beam of low-energy photons, it is known from U.S. Pat. No. 4,788,852 to use an emitting device comprising a radioactive source emitting at least two distinct energies or, alternatively, a device comprising several sources each emitting at a given energy.

However, it can be difficult to manufacture a single source reliably emitting at different energies, and it is tedious to use a device provided with several sources, in particular in the context of an oil installation.

One aim of the invention is to have an emitting device capable of simply generating both a beam of high-energy photons and a beam of low-energy photons using a single radioactive source, and if possible capable of nevertheless guaranteeing close beam intensities to obtain good precision in measuring the phase fractions of a polyphase fluid.

To that end, the invention relates to a device of the aforementioned type, characterized in that it comprises:

a target placed opposite the source, the target being capable of creating the second beam through interaction with a first portion of the high-energy photons of the incident beam coming from the source, a second portion of the photons of the incident beam coming from the source passing through the target to form the first beam.

The device according to the invention can comprise one or several of the following features, considered alone or according to all technically possible combinations:

it comprises a collimator inwardly having a central passage extending along a longitudinal axis, to orient the first beam and the second beam along the longitudinal axis towards a detector through the fluid;

the collimator defining at least one auxiliary passage for guiding the second beam towards the detector, the or each auxiliary passage extending around and away from the central passage and emerging upstream opposite the target;

the or each auxiliary passage extends along an auxiliary passage axis, the auxiliary passage axis and the longitudinal axis forming a non-zero angle projected in a plane passing through the longitudinal axis;

the target is pressed on the collimator and closes the central passage and the or each auxiliary passage;

the or each auxiliary passage is inwardly defined by at least one wall of the collimator capable of reacting with a high-energy photon to create a lower-energy photon;

the or each auxiliary passage has a transverse section larger than or equal to the transverse section of the central passage;

the cumulative transverse section of the or each auxiliary passage assumes a ring shape extending around the central passage;

the target comprises a central portion extending substantially perpendicular to the longitudinal axis and a peripheral portion diverging away from the collimator towards the source;

the peripheral portion of the target opens along an angle between 30° and 60°; and the device comprises a concentration member for concentrating the high-energy photons emitted by the source, the concentration member being arranged around the source, the concentration member having a downstream surface diverging around the source towards the collimator and capable of reacting with a high-energy photon to create a lower-energy photon.

The invention also relates to an assembly for measuring a polyphase fluid, contained in a pipe, characterized in that it comprises:

a measuring section connected to the pipe, the measuring section defining a measuring zone of the polyphase fluid;

a device as described above; and a detection sensor, the measuring zone being inserted between the target and the detection sensor, the device being capable of orienting the first beam and the second beam through the measuring zone towards the detection sensor.

The assembly according to the invention can comprise the following feature:

the detection sensor comprises a crystal capable of receiving the photons from the first beam and the second beam after their passage in the measuring zone, the crystal having an average atomic number of less than 40, the crystal advantageously being made with a base of yttrium aluminum perovskite or calcium fluoride.

The invention relates to a method for measuring a polyphase fluid contained in a pipe using an assembly as defined above, characterized in that it comprises the following steps:

arranging the polyphase fluid to be measured in the measuring zone of the measuring section;

activating the single source to create a single incident beam of high-energy photons oriented towards said target;

interaction between a first portion of the high-energy photons from the single incident beam and the target to create, after passage through the target, a first beam of high-energy photons and a second beam of low-energy photons;

guiding the first beam and the second beam to illuminate the fluid circulating in the measuring zone with the first beam and the second beam; and detecting, using the detecting sensor, the high-energy photons and low-energy photons from the first beam and the second beam, respectively, after their passage in the fluid.

The method according to the invention can comprise the following feature:

the device comprises:

a collimator inwardly having a central passage extending along a longitudinal axis, to orient the first beam and the second beam along the longitudinal axis towards a detector contained in the detection sensor through the fluid;

the collimator defining at least one auxiliary passage for guiding the second beam towards the detector, the or each auxiliary passage extending around and away from the central passage and emerging upstream opposite the target; and the guiding of the first beam being done through the central passage and the guiding of the second beam being done through the central passage and the or each auxiliary passage.

The invention also relates to an assembly for measuring phase fractions of a polyphase fluid contained in a pipe, characterized in that it comprises:

a measuring section connected to the pipe, the measuring section defining a measuring zone of the polyphase fluid;

a device for emitting a first beam of high-energy photons and at least one second beam of lower-energy photons intended to measure a fluid, comprising a radioactive source, a detection sensor, the measuring zone being inserted between the source and the detection sensor, the device being capable of orienting the first beam and the second beam through the measuring zone towards the detection sensor, and in that the detection sensor comprises a crystal capable of receiving the photons from the first beam and the second beam after their passage in the measuring zone, the crystal having an average atomic number of less than 40, the crystal advantageously being made with a base of yttrium aluminum perovskite or calcium fluoride.

The emitting device of this assembly does not necessarily comprise a single source or a target, but can comprise one or several of the features defined above.

The invention will be better understood upon reading the following description, provided solely as an example, and done in reference to the appended drawings, in which.

In all of the following, the terms "upstream" and "downstream" are used relative to the general direction of circulation of the photons from the source towards the detector.

Thus, the term "downstream" is generally understood as farther from the source and closer to the detector, while the term "upstream" is generally understood as closer to the source and farther from the detector.

A first measuring assembly 10 according to the invention is shown in FIGS. 1 to 4. This assembly 10 is intended to measure the different phase fractions of a polyphase fluid present in a pipe 12 of an exploitation installation of that fluid. During the measurement, the fluid can circulate in the pipe 12 or on the contrary be static in the pipe 12.

The installation is, for example, a hydrocarbon production well such as an oil or natural gas well.

The pipe 12 comprises a measuring section 20 on which the measuring assembly 10 is mounted. In the example illustrated in FIG. 1, the measuring section 20 has a vertical axis A-A'.

The polyphase fluid circulating in the pipe 12 is advantageously a mixture of hydrocarbons generally comprising a gaseous phase, an oily liquid phase, and an aqueous liquid phase.

Figure 1:
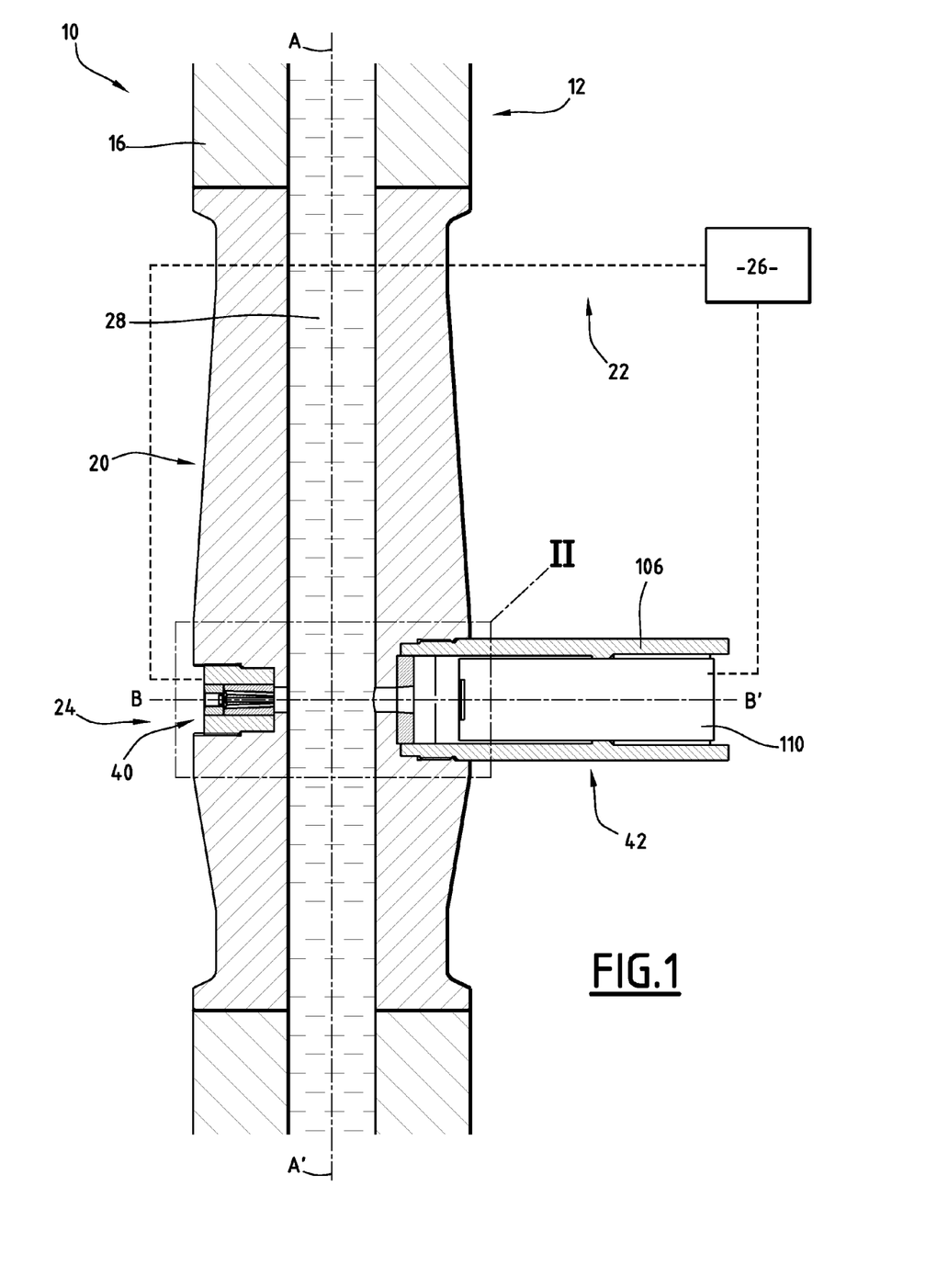
FIG. 1 is a cross-sectional view along a median vertical plane of a first measuring assembly according to the invention, mounted on a measuring pipe for polyphase fluid.

The measuring assembly 10 comprises a measuring section 20 forming a gamma measurement device 24 and a control and computation unit 26.

The measuring section 20 defines an inner passage 28 for measuring the fluid, with axis A-A'.

The gamma measuring device 24 comprises a first emitting device 40 capable of creating a first beam of high-energy photons and a second beam of lower-energy photons to transversely illuminate the polyphase fluid present in the circulation passage 28. It also comprises a sensor 42 for detecting photons from the first beam and the second beam recovered after their passage through the polyphase fluid.

Figure 2:
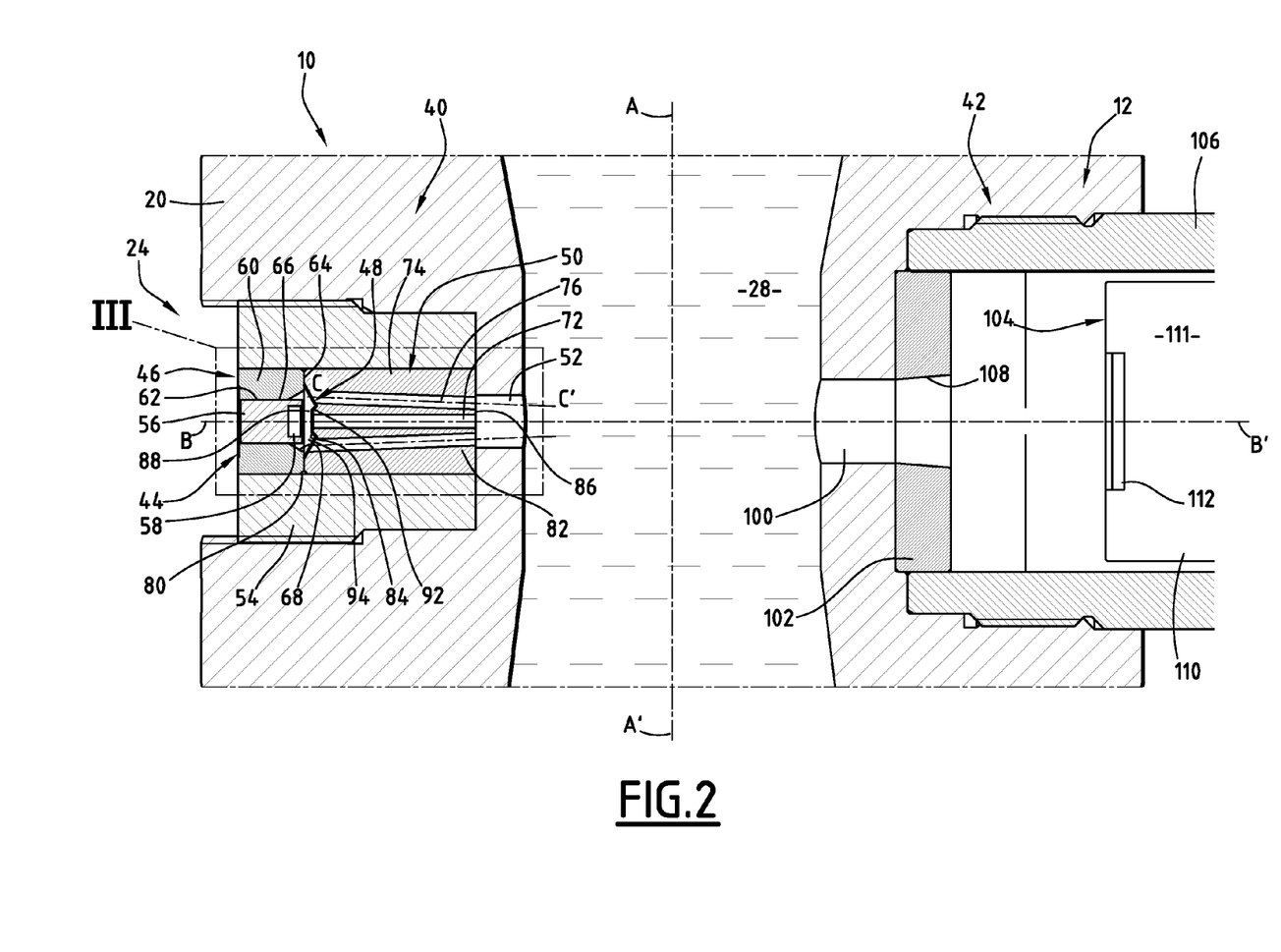
FIG. 2 is a view of a detail marked II in FIG. 1.
Figure 3:
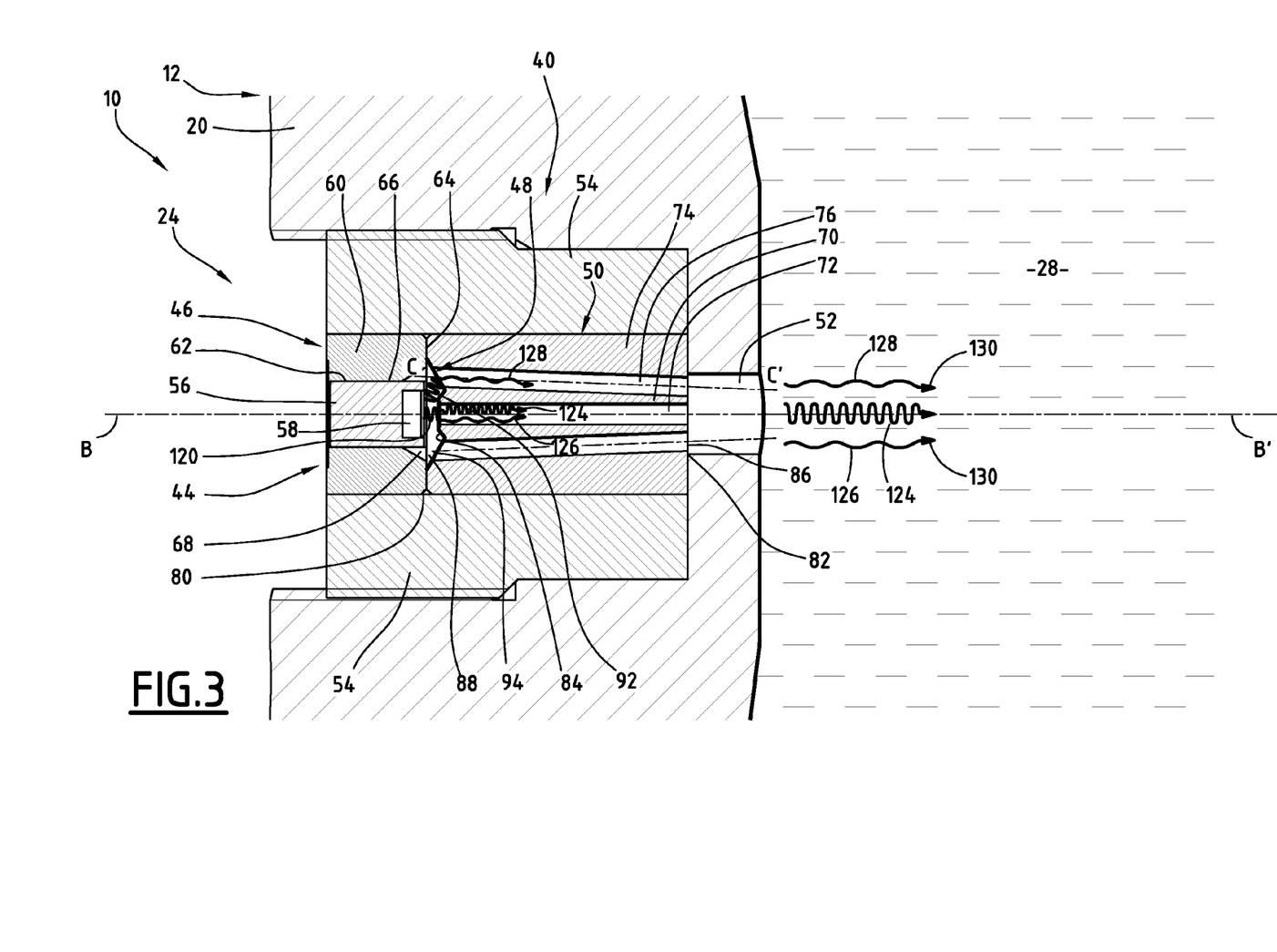
FIG. 3 is a view of a detail marked III in FIG. 2, illustrating a first device for emitting a beam of photons according to the invention.

As illustrated by FIGS. 2 and 3, the first emitting device 40 is arranged in a wall of the measuring section 20. It extends along a longitudinal horizontal axis B-B' that is substantially perpendicular to the axis A-A' of the passage 28.

The emitting device 40 comprises, from upstream to downstream, from left to right in FIG. 2 and FIG. 3, a single radioactive source 44, a radiation concentrator 46 arranged around the source 44, a target 48 capable of interacting with an incident beam created by the source 44 to create high-energy gamma photons and low-energy X photons, and a collimator 50 capable of orienting the beams of photons created at the outlet of the target 48.

The emitting device 40 also comprises a downstream protective window 52 intended to come into contact with the polyphase fluid circulating in the passage 28, and a peripheral support sleeve 54 of the source 44, the concentrator 46, and the collimator 50 in the wall of the section 20.

In reference to FIG. 3, the source 44 comprises a cylindrical capsule 56 for support and protection, and a radioactive pellet 58 mounted in a downstream housing formed at the end of the cylindrical body 56.

The capsule 56 and the pellet 58 are mounted coaxially along the axis B-B'.

The pellet 58 is advantageously made with a base of a radioactive material spontaneously emitting gamma photons. This material is advantageously Americium 241.

The radioactive source 44 is thus able to emit, spontaneously and permanently, over a solid angle greater than $2\pi$ sr centered around the axis B-B', an incident beam of high-energy gamma photons.

"High-energy gamma photons" refers in particular to gamma photons having an energy greater than 40 KeV and advantageously between 40 KeV and 100 KeV.

The pellet 58 generally has a diameter smaller than 10 mm, and for example between 3 mm and 7 mm, in particular equal to 5 mm.

The concentrator 46 is formed by a peripheral ring 60 extending around the source 44. The peripheral ring 60 has a peripheral inner surface 62 with axis B-B' defining a housing for inserting the source and emerging upstream and downstream of the ring 60. It also has a downstream edge 64 bearing on the collimator 50.

The inner surface 62 comprises a central region 66 pressed on the periphery of the source 44 to keep it in position along the axis B-B' and a downstream photon concentration region 68 that diverges radially around and away from the source 44 while being oriented towards the collimator 50.

The downstream region 68 is advantageously formed from or coated with a metal capable of interacting with the high-energy gamma photons created by the source 44 to create lower-energy X photons, hereinafter referred to as low energy photons. "Low energy" refers to photons having an energy 30% lower than that of the high-energy photons and in particular below 40 KeV, and advantageously between 15 KeV and 30 KeV.

The downstream region 68 is substantially in the shape of a truncated cone that opens forming an angle, in projection in a plane passing through the axis B-B' between 20° and 60°, and in particular equal to 30°.

The collimator 50 has a generally elongated cylindrical shape along the axis B-B'.

It comprises an inner annular wall 70 extending around the axis B-B', which defines a central passage 72 for collimating the first beam and part of the second beam.

According to the invention, the collimator 50 also comprises an outer peripheral wall 74 converging inwardly towards the downstream and defining, with the inner peripheral wall 70, a plurality of auxiliary passages 76 for collimating the second low-energy beam, the passages 76 being separated from each other by radial connecting walls 78 between the outer peripheral wall 74 and the inner peripheral wall 70.

The outer peripheral wall 74 extends between an upstream edge 80 pressed on the downstream edge 64 of the concentrator 46 and a downstream edge 82 advantageously pressed against the window 52.

The inner peripheral wall 70 extends between an upstream edge 84 axially offset in the downstream direction relative to the upstream edge 80 of the outer peripheral wall 74, and a downstream edge 86 situated at the downstream edge 82 of the outer peripheral wall 74, substantially in the same plane perpendicular to the axis B-B'.

The walls 70, 74 thus define, between the upstream edge 80 of the outer wall and the upstream edge 84 of the inner wall, a cavity 88 for receiving the target 48 situated opposite the source 44.

The insertion housing of the source 44 in the ring 62 emerges downstream in the cavity 88, opposite the downstream region 68.

The central passage 72 extends axially along the axis B-B' between the upstream edge 84 and the downstream edge 86 of the inner peripheral wall 70. It emerges upstream in the cavity 88 and downstream opposite the window 52. The central passage 72 has a constant transverse section, considered perpendicular to the axis B-B'.

The diameter of the central passage 72 is 60% smaller than the diameter of the source. It is for example between 1 mm and 3 mm.

The auxiliary passages 76 extend in the annular space delimited between the walls 70, 74. The passages 76 have, as illustrated in FIG. 4, a generally ring-shaped cumulative section extending around the axis B-B'.

Each auxiliary passage 76 extends in an angular sector defined by two adjacent radial walls 78 around the axis B-B'.

Figure 4:
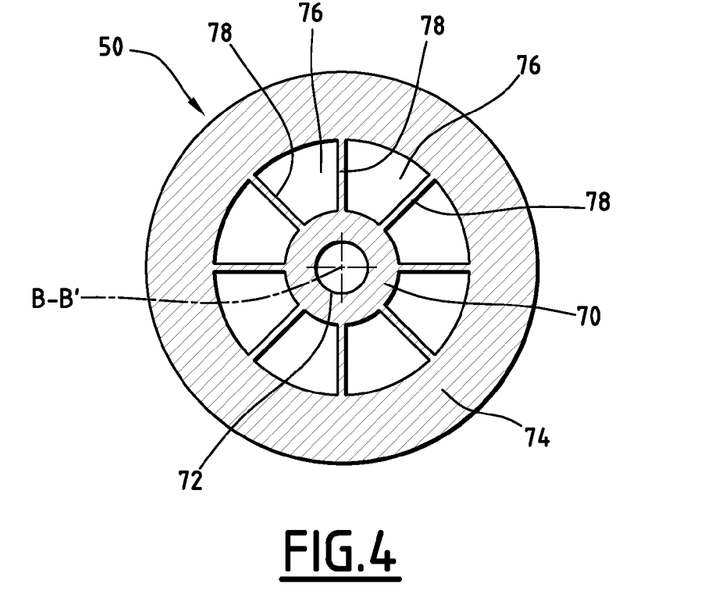
FIG. 4 is an end view of the downstream end of the collimator of the emitting device illustrated in FIG. 3.

In the example shown in FIG. 4, the number of auxiliary passages 76 around the axis B-B' is equal to 8. This number is more generally between 1 and 10.

As illustrated by FIG. 4, the transverse section of each auxiliary passage 76, considered perpendicular to the axis B-B', is greater than or equal to the transverse section of the central passage 72.

Moreover, each passage 76 has, projected in an axial plane passing through the axis B-B', an auxiliary passage axis C-C' that forms a non-zero angle with the longitudinal axis B-B', projected in the same plane.

This angle is advantageously greater than 0° and is between 2° and 3°.

The walls 70, 74 and 78 defining each passage 76 are advantageously coated with or formed from a metal capable of absorbing high-energy gamma photons to interact with these photons, and reemitting lower-energy X photons, as defined above.

In the example shown in FIG. 4, the radial walls 78 have a small thickness. Thus, the transverse section of each radial wall 78, considered in a plane perpendicular to the axis B-B', is smaller than at least twice, advantageously ten times the transverse section of an auxiliary passage 76.

In this example, the radial walls 78 extend over the entire length of the inner wall 70 considered along the axis B-B'.

In this example, the target 48 is pressed against the upstream edge 80 of the outer peripheral wall 74 of the collimator and against the upstream edge 84 of the inner peripheral wall 70.

The target 48 is made with a base of a thin metal sheet. Thus, the thickness of the sheet is smaller than the thickness of the source 58, considered along the axis B-B'. This thickness is chosen to be fine enough for at least 20% of the high-energy photons coming from the source 44 to pass through the sheet without interacting therewith.

The target 48 has a general solid tapered cup shape, having a central wall 92 perpendicular to the axis B-B' and a peripheral wall 94 substantially in the shape of a truncated cone.

The target 48 and its walls 92, 94 are made in a single piece from a metal similar or identical to that forming or coating the walls 70, 74, 78 defining the auxiliary passages 76. Thus, the material forming the target 48 is capable of at least partially absorbing the high-energy gamma photons produced by the incident beam resulting from the source 44 by photoelectric effect with the sheet whereof the atoms are de-excited by X fluorescence. This forms, after de-excitation by X fluorescence, lower-energy X photons, as defined above.

The central wall 92 is pressed against the upstream end 84. It completely closes the central passage 72 in the upstream direction. It extends opposite the source 44 in the cavity 88.

In this example, the central wall 92, and more generally the target 48, are situated completely away from the source 44. Alternatively, the source 44 is pressed against the central wall 92.

The peripheral wall 94 diverges towards the source 44 between the upstream edge 84 of the inner wall 70 and the upstream edge 80 of the outer wall 74. It completely closes each auxiliary passage 76.

The opening angle of the peripheral wall 94 is greater than 45° and is for example between 45° and 90°.

The fastening sleeve 54 surrounds the ring 60 and the collimator 50. It keeps those elements in position relative to each other. It is removably mounted in the wall of the section 20.

The upstream window 52 is sealably mounted between the downstream edge of the walls 70, 74 of the collimator 50 and the flow passage 28, to prevent the polyphase fluid from leaving the passage 28. It is substantially flush with the wall of the section 20 in the measuring passage 28. It extends around the axis B-B' and is made with a base of a material substantially transparent to photons, such as PEEK (PolyEtherEtherKetone), Beryllium, or Boron Carbide.

The detection sensor 42 is placed along the axis B-B' opposite the emitting device 40 relative to the passage 28 in the wall of the section 20. It comprises a downstream window 100, a downstream collimator 102, and a photon detector 104 that is supported by a support assembly 106.

The downstream window 100 extends around the axis B-B' in the wall of the measuring section 20 opposite and facing the upstream window 52 relative to the flow passage 28. It is flush with the wall of the section 20 in the passage 28.

The downstream collimator 102 defines a central opening 108 for passage of the first beam and the second beam.

The downstream detector 104 comprises a support body 110 containing instrumentation 111 and a crystal 112 for detecting photons.

The scintillation crystal 112 is capable of receiving the photons having passed through the fluid present in the passage 28 and restoring their energy in the form of visible light. It is preferably made with a base of a crystal having an average atomic number of less than 40.

This crystal is for example of the $T_nM_m$ type where T is a rare earth such as yttrium, M is a metal such as aluminum, and n and m are the respective valences of those elements. This crystal is advantageously doped with a lanthanide, such as cerium or europium. This crystal is for example yttrium aluminum perovskite doped with cerium (YAP:Ce).

Alternatively, this crystal is of the $A_nH_m$ type, where A is an alkaline earth metal such as calcium, H is a halogen such as fluorine, and n and m are the respective valences of these elements. This crystal is advantageously doped with a lanthanide such as cerium or europium. This crystal is for example $CaF_2$ doped with europium.

Generally, the crystal 112 is capable of receiving all of the energy of the high-energy photon radiation by interaction between the collected photon and an atom of the crystal emitting an X photon for shuffling the lower-energy atom. This photon is absorbed in turn in the crystal.

In certain cases, i.e. when the shuffling X ray leaves the crystal without interacting, the crystal only collects a fraction of the incident energy, the other fraction being carried away by the shuffling X ray, which escapes outside the crystal. There is then a risk of interpreting a high-energy photon measurement by that of a low-energy photon.

If the crystal is made with a base of the aforementioned materials whereof the exhaust energy is less than 15 keV, the high-energy photons will be collected between 60 keV and 40 keV, i.e. well above the low energy.

The crystal 112 is coupled to a photomultiplier tube capable of producing an electrical signal with an intensity representative of the light intensity emitted by the crystal. This signal is collected by the instrumentation 111.

The instrumentation 111 is connected to the control and computation unit 26. The unit 26 is capable of counting the number of photons per unit coming from the first high-energy beam and the number of photons coming from the second low-energy beam received on the detector 104.

A method for measuring the fractions $\alpha_g$, $\alpha_o$, $\alpha_w$ of the different phases of a polyphase fluid circulating in the passage 28 of the pipe 12 will now be described.

This method comprises arranging polyphase fluid in the passage 28.

When the respective sections $\alpha_g$, $\alpha_o$, $\alpha_w$ of the gaseous, aqueous liquid, and oily liquid phases must be determined, the emitting device 40 is activated. To that end, as illustrated in FIG. 3, the source 44 produces an incident beam 120 of high-energy gamma photons that spreads from the pellet 58.

The gamma photons of the incident beam 120 thus have an energy between 40 KeV and 100 KeV.

A large portion of the photons of this beam 120 goes towards the target 48 and collides with the central wall 92 and the peripheral wall 94 of the target 48, respectively.

A first portion of the high-energy photons having touched the central portion 92 does not interact with the material of the central portion 92 and passes through the central portion 92 while keeping their energy to form an incident beam of high-energy photons 124, which is oriented along the axis B-B' by its circulation in the central passage 72.

A second portion of the gamma photons of the incident beam 120 having hit the central wall 92 interacts with the material making up that central wall and loses energy to form a part 126 of a second beam of lower-energy X photons comprised, for example, between 15 KeV and 30 KeV.

These low-energy photons are guided in the central passage 72.

The number of low-energy photons in the central passage 72 is 10% lower than the number of high-energy photons in the central passage 72.

Moreover, part of the photons of the incident beam 120 emitted by the source 44 collides with the peripheral wall 94 of the target 48. Due to the incline of the peripheral wall 94 relative to the axis B-B' and the incidence angle of the incident photons, these high-energy photons interact mostly with the target 48 to form lower-energy photons. These lower-energy photons are guided in each auxiliary passage 76 to form an auxiliary beam 128 made up solely of low-energy photons.

At the outlet of the collimator 50, and before passage in the window 52, the first beam of high-energy photons 124 is guided by the central passage 72 and a resulting second global beam 130 of low-energy photons is obtained from the beam 126 of low-energy photons coming from the main passage 72 and auxiliary beams 128 coming from the auxiliary passages 76.

Thus, the number of low-energy photons illuminating the fluid in the flow passage 28 increases significantly to represent more than 40% of the number of high-energy photons illuminating the fluid in the flow passage 28. This proportion can also be adjusted by the choice of the diameter of the central passage 72.

Moreover, the material forming the walls defines the auxiliary passages 76 and the material forming the downstream region 68 of the concentrator captures high-energy photons and creates low-energy photons, which increases the intensity of the second beam 130.

The beams 124, 130 pass through the polyphase fluid through the passage 28, substantially along the axis B-B', transversely relative to the axis A-A' of circulation of the fluid in the passage 28. During this crossing, they interact mainly through photoelectric absorption and Compton scattering with the different phases of the polyphase fluid present in the passage 28.

The high-energy and low-energy photons of the beams 122, 130 then penetrate through the downstream window 100, then through the opening 108 in the detection sensor 42. They are collected on the crystal 112 of the detector 104, where they create signals of an amplitude that is representative of the collected energy.

The instrumentation 111 then collects signals representative of these amplitudes and provides the control and computation unit 26 with a set of impulses measured as a function of time by the measuring means. The unit 26 then builds a spectrum in which the high-energy photons and the low-energy photons are distributed as a function of their energy.

The unit 26 then determines the fractions of the different phases of the polyphase fluid, for example using a system of equations connecting the number of counts of high-energy photons received on the detector 104 and the number of low-energy photons received on the detector 104 per unit of time, calibration coefficients, and the sections $\alpha_g$, $\alpha_o$, $\alpha_w$.

The measuring assembly 10 according to the invention thus comprises a device 40 for emitting a beam 130 of low-energy photons and a beam 124 of high-energy photons that uses a single radioactive source 44, which makes it easier and safer to manipulate on a worksite.

Despite the use of this single source 44, the relative intensities of the beam of high-energy photons 124 and the beam of low-energy photons 130 are not significantly different, which makes it possible to obtain a good measuring resolution. This result is obtained in particular by collecting a larger portion of the low-energy photons emitted by the target 48 and efficiently guiding them through the collimator 50 in the auxiliary passages 76.

Figure 5:
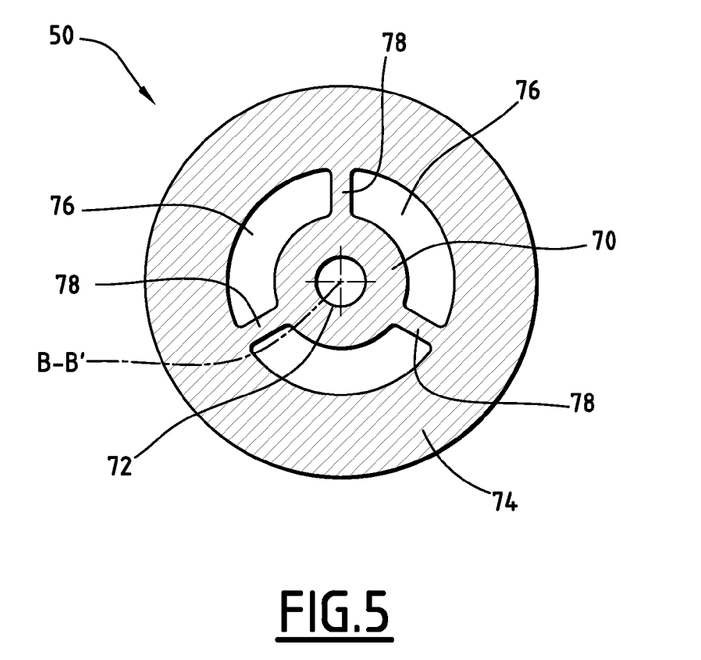
FIG. 5 is a view similar to FIG. 4 for a second emitting device according to the invention.

The downstream end of the collimator 50 of a second emitting device 40 according to the invention is shown in FIG. 5. Unlike the first emitting device 40 shown in FIG. 4, this collimator 50 has three auxiliary passage passages 76 extending angularly over about 120° around the axis B-B'. The operation of this emitting device 40 is similar to that of the first emitting device 40.

Figure 6:
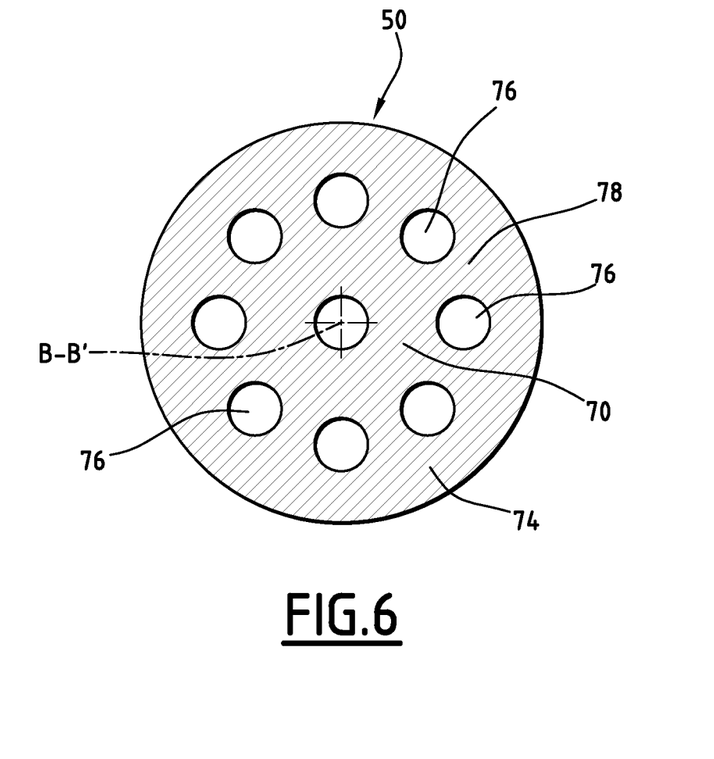
FIG. 6 is a view similar to FIG. 4 for a third emitting device according to the invention.

In the alternative shown in FIG. 6, the collimator 50 has auxiliary passages 74 formed by holes with a circular section distributed in rings around the axis B-B'.

Each auxiliary passage 76 in this case has a section substantially equal to that of the central passage 72.

In one alternative (not shown), the sheet of the target 48 is formed by a plurality of regions with a base of distinct metal materials. For example, the foil can comprise a plurality of metal layers formed with a base of distinct metals.

This makes it possible to create a plurality of beams 130 of lower-energy photons than the incident beam 120, with distinct energies that depend on the nature of the metal making up the different regions.

In one particular application, the measuring section 20 of the measuring assembly 10 constitutes a venturi having a neck. The passage 28 then has a lumen with a smaller diameter.

In that case, the measuring assembly 10 is advantageously provided with a differential pressure sensor to measure the pressure difference through the neck of the venturi.

The pipe 12 is then advantageously connected to a wellhead to collect the polyphase fluid extracted from the well.

In one alternative, the target 48 is capable of creating two beams of lower-energy photons, situated in distinct energy ranges, for example between 15 keV and 30 keV for a first low-energy beam and between 30 keV and 50 keV for an auxiliary low-energy beam.

In this case, the target 48 advantageously comprises a first region formed with a base of a first metal, and a second region formed with a base of a second metal distinct from the first metal.

Thus, the target 48 for example has a central wall 92 formed from the first metal and a peripheral wall 94 formed from the second metal.

The central wall 92 is capable of forming the low-energy photons of the first low-energy beam by fluorescence, and the peripheral wall 94 is capable of forming the photons of the low-energy auxiliary beam by fluorescence.

In this alternative, the incident beam 120 hits the target 48 both in the central wall 92 and in the peripheral wall 94. A first part of the gamma photons of the incident beam 120 interacts with the first metal contained in the central wall 92 and forms a first beam of lower-energy X photons in a first low-energy interval, for example between 15 keV and 30 keV.

The other part of the photons of the incident beam 120 interacts with the second metal contained in the peripheral portion 94 and creates an auxiliary beam of lower-energy X photons in a lower-energy auxiliary interval, for example between 30 keV and 60 keV.

The high-energy beam and the two lower-energy beams illuminate the fluid in the flow passage and are collected in the detection sensor 42 to be measured and create amplitude signals representative of the collected energy.

It is thus possible to determine not only the sections $\alpha_g$, $\alpha_o$, and $\alpha_w$ as described above, but also another parameter such as, for example, a property of one of the phases (for example salinity of the water, sulfur concentration of the oil) or the fraction of a fourth phase present in the circulating fluid, like a suspended solid phase, such as sand, directly.

A method for measuring salinity from photons collected in a third energy interval is for example described in U.S. Pat. No. 5,854,820.

In another alternative, the target 48 is formed by a multi-layer assembly of metal sheets, at least one first layer being formed from a first metal, at least one second layer being formed from a second metal.

In one alternative, the metal layer is formed from an alloy of the first metal and the second metal.

The invention claimed is:

1. A device for emitting a first beam of high-energy photons and at least one second beam of lower-energy photons, comprising:
   a single radioactive source, suitable for generating an incident beam of high-energy photons;
   a target placed opposite the radioactive source, the target being capable of creating the at least one second beam through interaction with a first portion of the high-energy photons of the incident beam coming from the source a second portion of the photons of the incident beam coming from the source passing through the target to form the first beam; and
   a collimator inwardly having a central passage extending along a longitudinal axis, to orient the first beam and the second beam along the longitudinal axis towards a detector through a fluid, the collimator defining at least one auxiliary passage for guiding the second beam towards the detector, the at least one auxiliary passage extending around and away from the central passage and emerging upstream opposite the target.

2. The device according to claim 1, wherein the at least one auxiliary passage extends along an auxiliary passage axis, the auxiliary passage axis and the longitudinal axis forming a non-zero angle projected in a plane passing through the longitudinal axis.

3. The device according to claim 1, wherein the target is pressed on the collimator and closes the central passage and the at least one auxiliary passage.

4. The device according to claim 1, wherein the at least one auxiliary passage is inwardly defined by at least one wall of the collimator capable of reacting with a high-energy photon to create a lower-energy photon.

5. The device according to claim 1, wherein the at least one auxiliary passage has a transverse section larger than or equal to the transverse section of the central passage.

6. The device according to claim 5, wherein the cumulative transverse section of the at least one auxiliary passage (76) assumes a ring shape extending around the central passage.

7. The device according to claim 1, wherein the target comprises a central portion extending substantially perpendicular to the longitudinal axis and a peripheral portion diverging away from the collimator towards the source.

8. The device according to claim 7, wherein the peripheral portion of the target opens along an angle between 30° and 60°.

9. The device according to claim 1, further comprising a concentration member for concentrating the high-energy photons emitted by the source, the concentration member being arranged around the source, the concentration member having a downstream surface diverging around the source towards the collimator and capable of reacting with a high-energy photon to create a lower-energy photon.

10. The device according to claim 1, wherein the first beam is formed from photons having an energy comprised in a first energy interval, the second beam being formed from photons having an energy comprised in a second energy interval lower than the first energy interval, the target being capable of creating a second auxiliary beam of lower-energy photons having an energy comprised in an auxiliary energy interval distinct from the second energy interval and the first energy interval.

11. The device according to claim 1, wherein that the target comprises at least one first region made from a first metal, capable of creating lower-energy photons intended to form the second beam, and a second region formed from a second metal, distinct from the first metal, capable of forming lower-energy auxiliary photons, forming the second auxiliary beam.

12. An assembly for measuring phase fractions of a polyphase fluid contained in a pipe, comprising:
 a measuring section connected to the pipe, the measuring section defining a measuring zone of the polyphase fluid;
 a device according to any one of the preceding claims; and
 a detection sensor, the measuring zone being inserted between the target and the detection sensor, the device being capable of orienting the first beam and the second beam through the measuring zone towards the detection sensor.

13. The assembly according to claim 12, wherein the detection sensor comprises a crystal capable of receiving the photons from the first beam and the second beam after their passage in the measuring zone, the crystal having an average atomic number of less than, the crystal advantageously being made with a base of yttrium aluminum perovskite or calcium fluoride.

14. A method for measuring a polyphase fluid contained in a pipe using an assembly according to one of claims 12, comprising:
 arranging the polyphase fluid to be measured in the measuring zone of the measuring section;
 activating the single source to create a single incident beam of high-energy photons oriented towards said target;
 interaction between a first portion of the high-energy photons from the single incident beam and the target to create, after passage through the target, a first beam of high-energy photons and a second beam of low-energy photons;
 guiding the first beam and the second beam to illuminate the fluid circulating in the measuring zone with the first beam and the second beam; and
 detecting, using the detecting sensor, the high-energy photons and low-energy photons from the first beam and the second beam, respectively, after their passage in the fluid;
 the guiding of the first beam being done through the central passage and the guiding of the second beam being done through the central passage and the at least one auxiliary passage.

* * * * *